US 6,658,280 B1

(12) United States Patent
Haacke (10) Patent No.: US 6,658,280 B1
(45) Date of Patent: Dec. 2, 2003

(54) SUSCEPTIBILITY WEIGHTED IMAGING

(76) Inventor: E. Mark Haacke, 440 E. Ferry St. Unit 2, Detroit, MI (US) 48202

( * ) Notice: Subject to any disclaimer, the term of this patent is extended or adjusted under 35 U.S.C. 154(b) by 0 days.

(21) Appl. No.: 10/143,671

(22) Filed: May 10, 2002

(51) Int. Cl.⁷ .............................................. A61B 5/055
(52) U.S. Cl. ...................... 600/410; 600/407; 324/306; 324/307
(58) Field of Search ................................ 600/407, 410, 600/413, 419; 324/306, 307, 309

(56) References Cited

U.S. PATENT DOCUMENTS

| | | | |
|---|---|---|---|
| 5,273,040 A | 12/1993 | Apicella et al. | |
| 5,337,000 A | 8/1994 | Bruder | |
| 5,447,155 A | 9/1995 | NessAiver et al. | |
| 5,545,992 A | 8/1996 | Foo | |
| 5,668,474 A | 9/1997 | Heid | |
| 5,997,883 A | 12/1999 | Epstein et al. | |
| 6,034,528 A | 3/2000 | Heid | |
| 6,073,041 A | 6/2000 | Hu et al. | |
| 6,078,175 A | 6/2000 | Foo | |
| 6,246,897 B1 * | 6/2001 | Foo et al. | 600/413 |
| 6,434,412 B1 | 8/2002 | Simonetti et al. | |
| 6,501,272 B1 * | 12/2002 | Haacke et al. | 324/306 |

OTHER PUBLICATIONS

Kim et al. "Automatic Selection of Mask and Arterial Phase Images for Temporarily Resolved MR Digital Subtraction Angiography," Magnetic Resonance in Medicine 48:1004–1010 (2002).*

Westbrook et al., MRI in Practice, Blackwell Scientific Publications, 1993, pp. 102–131 and 200–203.

Heid, TrueFisp Cardiac Fluoroscopy 1997, Abstract Proceedings of the ISMRM, p. 320.

Wang et al., *J of Magnetic Resonance Imaging* 12:661–670, 2000.

Cox et al., *J of Magnetic Resonance Imaging* 70:163–168, 1986.

Yamada et al., *Radiology* 175:561–565, 1990.

Reichenbach et al., *Radiology* 204:272–277, 1997.

Reichenbach et al., *Magnetic Resonance Materials in Biology, Physics and Medicine* 6:62–69, 1998.

Gronemeyer et al., *JMRI* 2:271–276, 1992.

Ogg et al., *Magnetic Resonance Imaging* 17:8:1142–1148, 1999.

Ogg et al., *MRM* 40:749–753, 1998.

Haacke et al., "Susceptibility Weighted Imaging (SWI): A new means to enhance image contrast" The MR Institute for Biomedical Research 8706 Manchester Road, Suite 102, St. Louis Missouri 63144, St. Jude's Children's Research, 332 N. Lauderdale, Memphis, Tennessee 38105and University of Jena.

* cited by examiner

Primary Examiner—Marvin M. Lateef
Assistant Examiner—Barry Pass
(74) Attorney, Agent, or Firm—Fish & Richardson P.C.

(57) ABSTRACT

A method for magnetic resonance imaging is described.

26 Claims, 5 Drawing Sheets

- Choose echo time, TE, for partial volume signal cancellation
- Collect Data

210

- Compute a Phase Image.

220

- (Optionally) Collect data at a second echo time to produce a Corrected Phase Image.

230

- Choose Filter.
- Process Phase Data with Filter and Compute a Local Phase Image.
- (Optionally) Display corrected, filtered phase image

240

- Compute Magnitude Image.

250

- Compute a Mask from the Phase Image
- Select q

260

- Apply Mask to Magnitude Image

| | |
|---|---|
| ■ Choose an echo time, TE, or set of echo times. | 310 |
| ■ Select a resolution higher than the features of interest.<br>■ Collect Data. | 320 |
| ■ Compute a Phase Image at the acquisition resolution. | 330 |
| ■ Choose Filter.<br>■ Process Phase Data with Filter and Compute a Local Phase Image at the acquisition resolution. | 340 |
| ■ Compute a Magnitude Image at the acquisition resolution. | 350 |
| ■ Combine acquisition resolution magnitude and phase images to reconstruct new phase and magnitude images at lower resolutions. | 360 |
| ■ Compute a Mask from the new Phase Image in Step 360<br>■ Select q | 370 |
| ■ Apply Mask to Magnitude Image from Step 360<br>■ Repeat multiple times at different resolutions | 380 |

FIG. 4

SUSCEPTIBILITY WEIGHTED IMAGING

TECHNICAL FIELD

This invention relates to magnetic resonance imaging.

BACKGROUND

Magnetic resonance (MR) imaging is a useful noninvasive method for imaging the internal components of a wide array of objects. Its noninvasive imaging of tissue in living subjects, especially humans, is highly valued in the medical field.

In its most basic form, MR imaging measures nuclear spin density throughout a sample. In this case, the image intensity is proportional to the number of observed nuclear spins. Practically, either the spin density, $T_1$ or $T_2$ of $^1H$ nuclei is measured. Although such images provide valuable information about an object, these parameters alone may not provide adequate image contrast. Many dissimilar materials have very similar spin densities, $T_1$ or $T_2$ and, therefore, such materials are indistinguishable or in other words they lack contrast.

A technique for enhancing contrast is described in "Artery and Vein Separation Using Susceptibility-Dependent Phase in Contrast-Enhanced MRA", Wang et al., Journal of Magnetic Resonance Imaging, 12:661–670 (2000), the entire contents of which is incorporated herein by reference. In this technique, a magnitude and phase image are obtained using a gradient echo sequence. The magnitude image is operated upon using a mask computed from the phase image.

SUMMARY

In one aspect the invention features a method of MR imaging, including: obtaining a magnitude image, obtaining a phase image, computing a phase image mask using the phase image, applying the phase image mask to the magnitude image a number q times, and selecting q by computing CNR as a function of q.

In another aspect, the invention features a method of MR imaging including: computing CNR as a function of q, SNR, and $\Delta\phi$, and selecting q, SNR and $\Delta\phi$ to produce a desired CNR.

In another aspect the invention features a method of MR imaging, including: obtaining a phase image and applying minimum intensity projection to the phase image.

In another aspect, the invention features a method of MR imaging, including: obtaining a first phase image by selecting a first echo time, obtaining a second phase image by selecting a second echo time, obtaining a predicted phase image by extrapolating the first phase image to the second echo time, and computing a corrected phase image by computing the difference between the predicted phase image and second phase image.

In another aspect the invention features a method of MR imaging including: obtaining a magnitude image, obtaining a phase image, computing a phase image mask using the phase image, applying the phase image mask to the magnitude image a number q times, selecting an acquisition resolution such that the resolution is higher than the size of a feature of interest, and wherein obtaining a magnitude and obtaining a phase image comprises reconstructing a magnitude and a phase image at a lower resolution than the resolution of the acquired data.

Embodiments of the method may include one or more of the following features.

The method may compute CNR as a function of SNR and $\Delta\phi$. The method may compute CNR using $CNR(q)=SNR*(1-(1-|\Delta\phi|/\pi)^q)/\sqrt{1+q^2/\pi^2}$. $\Delta\phi$ may be the phase difference between water and fat. $\Delta\phi$ may be the phase difference between tissues with different amounts of iron.

The method may select q by using a function dependent on the size of a feature of interest. The method may select q such that $\sqrt{A}\,CNR(q)$ is greater than a value in the range from about 3 to about 5 where A is the area of the feature of interest measured in square pixels.

The method may include selecting a filter for reducing nonlocal contributions to the phase image, computing a local phase image by filtering the first phase image with the filter to reduce nonlocal contributions on the image, and wherein computing a phase image mask further includes using the local phase image.

Obtaining the magnitude and phase image may include selecting a first echo time that results in partial volume cancellation of features of interest. The method may include obtaining images of veins. The method may include obtaining images of microhemorrage.

The method may include obtaining a second phase image by selecting a second echo time that results in partial volume cancellation of features of interest, computing a corrected phase image by using the first and second phase images, and the computing the phase image mask includes using the corrected phase image.

The method may include selecting an acquisition resolution such that the resolution is higher than the size of a feature of interest, and acquiring magnitude and phase data at the acquisition resolution. Obtaining a magnitude and obtaining a phase image may include reconstructing a magnitude and a phase image at a lower resolution than the resolution of the acquired data. Reconstructing a magnitude and a phase image may include using the magnitude data and the phase data.

The method may include selecting a filter for reducing nonlocal contributions to the phase data, computing local phase data by filtering the phase data with said filter to reduce nonlocal contributions on the phase data, and reconstructing the magnitude and the phase image inlcudes using the magnitude data and the local phase data.

The method may include selecting an echo time to produce the selected SNR or $\Delta\phi$. The method may include selecting a set of echo times to produce the selected SNR or $\Delta\phi$. The method may compute CNR as $CNR(q)=SNR*(1-(1-|\Delta\phi|/\pi)^q)/\sqrt{1+q^2/\pi^2}$. The desired CNR may be defined such that $\sqrt{A}\,CNR(q)$ is greater than a value in the range from about 3 to about 5 where A is the area of the feature of interest measured in square pixels. CNR may be dependent on the number of data acquisitions and the method may include selecting a number of data acquisitions to produce the desired CNR.

The method may include for a given total data acquisition time, selecting a number of data acquisitions. The method may compute CNR according to $CNR(q)=SNR*\sqrt{1/\alpha}*\exp((1-\alpha)TE/T_2^*)*(1-(1-|\Delta\phi|/\pi)^q)/\sqrt{1+q^2/\pi^2}$ wherein $\alpha=\Delta\phi/\pi$. SNR and $\Delta\phi$ may depend on partial volume cancellations.

The method may include selecting a filter for reducing nonlocal contributions to the corrected phase image, and computing a local phase image by filtering the first phase image with said filter to reduce nonlocal contributions on said corrected phase image.

Embodiments may include one or more of the following advantages. An advantage of embodiments is improved contrast in magnetic resonance imaging. Using this method an imaging experiment can be optimized by determining the contrast-to-noise ratios (CNR) of a final image as a function of the signal to noise ratio of the magnitude image (SNR), the phase difference between objects of interest (Δφ), and the number of times (q) a phase mask is applied to the magnitude image. This permits selection of an optimal value of q to maximize CNR for given experimental conditions. For example, a given phase difference between features of interest may vary between different experiments due to hardware limitations, relaxation times, or susceptibility of the features of interest, yet the analysis determines a value of q that optimizes CNR in a final susceptibility weighted image in each of these cases. Alternatively, or in addition, given a target CNR the analysis provides experimental and processing parameters including echo time and multiplier q that most likely will result in a final image with the target CNR.

The entire contents of U.S. patent application Ser. No. 09/098,651, filed Jun. 17, 1998 and entitled "Application-specific optimization of echo time in MR pulse sequences for investigating materials with susceptibilities different from that of the background in which they are embedded" is incorporated herein by reference.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
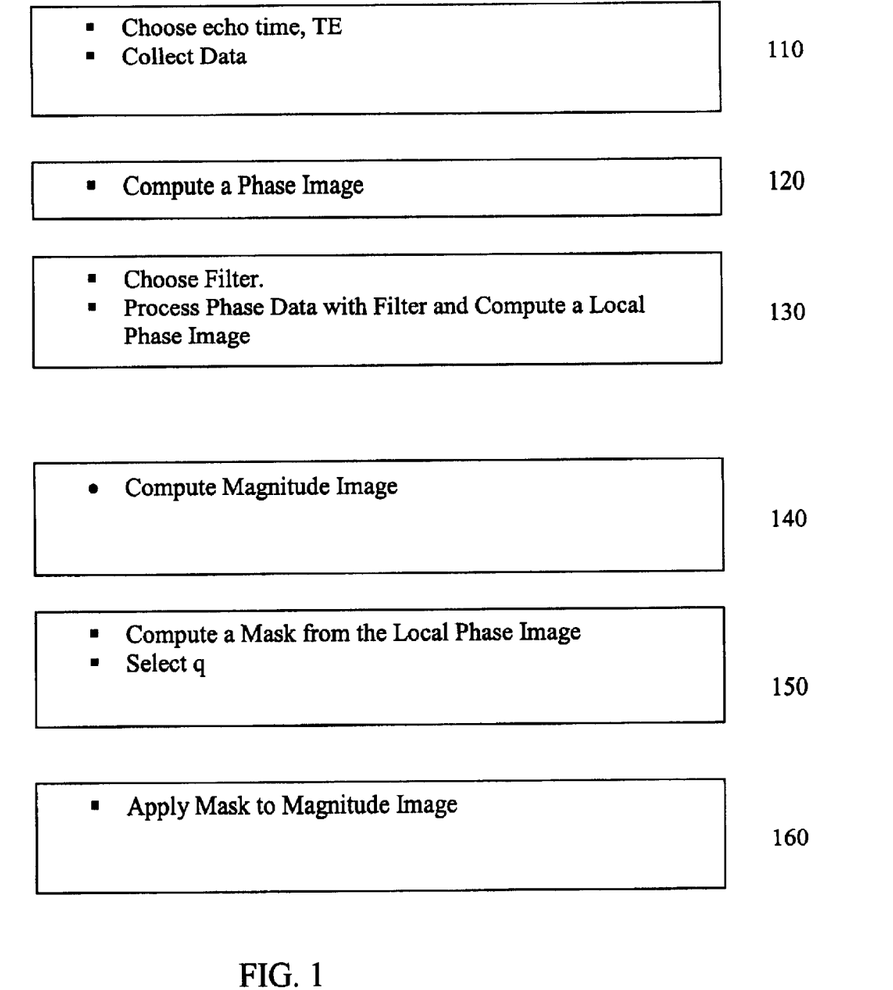
FIG. 1 is a diagram that outlines a method for MR imaging that utilizes phase information.

FIG. 1 outlines an MR imaging method 100 that includes using phase information directly as an image or using phase information to enhance contrast in magnitude images. In step 110, the echo time of a gradient echo imaging pulse sequence, TE, is chosen such that the phase contrast between features of interest is sufficiently above noise levels. A MR imaging system collects the data using the imaging pulse sequence with the echo time TE. The acquired data is then processed in step 120 to create a phase image. A filter is applied to the phase image in step 130 to remove or reduce unwanted phase effects. The resulting phase image can itself be used for visualizing structures. For example, phase images of the brain often may themselves be useful. The original acquired data is processed again in step 140 to create a magnitude image. From this filtered image, a mask is created in step 150 which transforms the phase image into a set of values ranging between zero and unity and a multiplication exponent q is selected. The mask is then applied to the magnitude image q number of times in step 160 to enhance the contrast in the magnitude image. The number of times, q, is obtained by determining the CNR as a function of q. Each step will be described in more detail.

Step 110: An understanding of the sources of phase variation is useful in determining the optimum echo time. The phase of MR data from a gradient echo pulse sequence is given by $$\phi = -\gamma \Delta B_Z TE \quad [1]$$

where $\gamma$ is the gyromagnetic ratio, $\Delta B_Z$ is the variation in magnetic field from one tissue to the next, and TE is the echo time. For example, if two tissues of interest have a phase difference $\Delta\phi$ caused by their susceptibility difference, then under ideal conditions (i.e., ignoring $T_2$ effects) the optimal choice of TE is such that $\Delta\phi = \pi$ or $\Delta\phi = -\pi$. A more realistic method includes the signal decay due to $T_2$ effects. An example of such a method chooses the optimal TE by considering contrast-to-noise (CNR) between two tissues with a phase difference of $\Delta\phi$. The CNR is given by $$CNR(\Delta\phi) = S * \Delta\phi/\sigma \quad [2]$$

where $\sigma$ is the noise in the magnitude image and S is the signal in the magnitude image. S is proportional to $\exp(-TE/T_2)$ and $\Delta\phi$ is proportional to TE. The optimum echo time, $TE_{opt}$, is the echo time that maximizes the function $TE\exp(-TE/T_2)$. By setting the derivative of this function to zero and solving for TE, it is found that the optimum echo time $TE_{opt} = T_2$. This assumes that $T_2$ is the same for each of the two adjacent tissues. If the $T_2$ of the tissues differ, then the optimal choice of echo time lies somewhere between the two values and can be calculated by deriving a similar CNR function. However, this optimal echo time may be longer than necessary. If the TE is chosen so that the CNR is larger than 4 then the phase difference between the two tissues will be visible. The user can choose to go to the longer TE if better image quality is desired.

If there are many tissues present in the sample, TE may be chosen to allow all the data to be analyzed simultaneously. The user might, for example, choose $TE_{opt}$ equal to the shortest optimal TE and as long as this value yields a CNR greater than 4 for the other longer $T_2$ tissues then reasonable contrast is attained. Alternatively, the data can be collected as a series of images during a multi-echo pulse sequence and the images then processed yielding phase information at various echo times for each tissue.

Once TE is chosen, the MR data set is acquired. A suitable system for MR imaging is the Siemens Symphony (Siemens Corporation, Iselin, N.J.) with a field strength of 1.5T. As systems change in design or field strength, the steps described herein can be appropriately modified to accommodate such changes. A suitable pulse sequence is a 3D gradient echo pulse sequence.

Step 120: The acquired data are complex Fourier transformed to create a real (R(r)) and imaginary (I(r)) pair of images. These images are converted into a phase image $\phi(r)$ as follows:

$$\phi(r) = \arctan(I(r)/R(r)). \quad [3]$$

This step computes the phase image.

Step 130: As described in Eq. (1), the phase depends on $\Delta B_z(r)$. The field variation, $\Delta B_z(r)$, can be written as the sum of two components $$\Delta B_z(r) = \Delta B_z^0(r) + B_z^M(r). \quad [4]$$

The first term, $\Delta B_z^0(r)$, is representative of the inhomogeneity in the applied field although it can contain other effects such as off centered sampling of the data. Even with modern high homogeneity superconducting magnets and high order shimming, the applied main field varies throughout the sample volume. On a typical MR imaging system this field inhomogeneity, $\Delta B_z^0(r)$ is typically about 0.5 ppm across a patient's head, for example. The second term, $B_z^M(r)$, includes all the contributions from fields that are induced by the applied field. These include chemical shift and susceptibility effects.

Combining these two terms into Eq. [1], the phase of the MR signal is given by $$\phi = -\gamma TE[\Delta B_z^0(r) + B_z^M(r)]. \quad [5]$$

Thus the phase depends on both the field inhomogeneity and the magnetic field $B_z^M(r)$ at that point. The magnetic field at a point r due to the magnetizations depends on the susceptibility, $X_M(r')$, at every point r' in the sample. The filtering of step 120, reduces the contributions of the field inhomogeneities and the contributions from nonlocal susceptibility effects.

Generally, these undesired phase effects have low spatial frequency and are filtered out by applying a high pass spatial filter to the phase image $\phi(r)$. An appropriate filter size is chosen based on the given body part and magnet inhomogeneities. The filter reduces these unwanted field effects to zero or a satisfactory level. The high pass filter is then applied to create what is effectively a local phase image, $\phi_L(r)$. The filter not only removes the phase contributions from the field inhomogeneity $\Delta B_z^0(r)$ but also reduces most of the nonlocal contributions to the phase image, including those coming from the nonlocal sources of susceptibility.

For example, the sinuses in the brain can act like a local dipole. Far from this source the field varies slowly $$\cong \frac{1}{r^3}.$$

By applying a high pass filter that removes low spatial frequency variation, most of the slowly varying phase variations (such as the long distance effects of the example dipole field) are filtered out leaving the more local effects. A method to produce such high pass filtering uses first a low pass filter of the phase image. The low pass filtered image is complex divided into the original image thus producing a high pass filtered image. The size of the filter used depends on the echo time and the local fields present. For an average 1.5T system, and with an echo time of 40 ms, a filter size of 64×64 or 96×96 may be used to create the low pass filtered image. This image is then complex divided into the original phase image to create an effective high pass filtered image that is the local phase image $\phi_L(r)$. Experimentally, for a field-of-view of 256 mm, a resolution of 0.5 to 1.0 mm in each of two dimensions and a filter size of 96×96, all visible low frequency effects are gone but 80% of the local contrast remains intact for small objects around 5 mm in size. A higher contrast remains for the 64×64 filter, but there are more edge artifacts from the air/tissue interfaces that otherwise do not appear with a 96×96 filter.

Furthermore, because the phase is directly proportional to the echo time as shown in Eq. (1), when the echo time is reduced (increased) the filter size can be reduced (increased). For example using the above example, if instead a TE of 5 ms were used, then the filter size could be reduced to 8×8 or 16×16 and still effectively remove background field effects from air/tissue interfaces.

In addition, the choice of filter also depends on the susceptibility of the source. For example, if a filter size of 96×96 is chosen for TE=40 ms, and the images are acceptable to the clinician, and there is a fresh clot present in the image, then for data acquired at TE=5 ms, a smaller filter may be used. On the other hand, if an old clot with 8 times higher susceptibility due to the presence of a large concentration of hemosiderin is present, then an image acquired with a TE=5 ms would show the same signal changes in the magnitude and phase images as the longer echo TE=40 ms scan and, therefore, to filter out the low spatial frequency effect would require the same filter size as for the TE=40 ms case or 96×96. Larger (smaller) magnetic field variations would require a larger (smaller) filter size.

After this filter is applied, a new source of image contrast is provided: a filtered, local phase image. The phase image can be displayed and analyzed directly if desired. Alternatively, or in addition, contrast in the magnitude image is created by using the local phase image to create a phase mask and then multiply it against the magnitude image to create a susceptibility weighted image as described further below.

Step 140: The original acquired data are complex Fourier transformed to create a real (R(r)) and imaginary (I(r)) pair of images. These image are converted into a magnitude image, $\rho_m(r)$, as follows:

$$\rho_m(r) = \text{sqrt}(R(r)^2 + I(r)^2). \quad [8]$$

Step 150: The local phase image is used to compute a mask, $\phi_{MASK}(r)$. The mask takes on values between zero and unity for each pixel location. The filtered phase image contains susceptibility information (i.e., variations in phase) but these changes in phase need to be converted into a set of numbers that will enhance the contrast in the magnitude images. For example, a suitable mask is computed from the local phase image by, if $\phi_L(r) < \phi_0$ then $\phi_{MASK}(r) = 1$.

if $\phi_L(r) > \phi_0$ then $\phi_{MASK}(r) = 1 + (\phi_L(r) - \phi_0)/\pi$ [6]

where $\phi_0$ is a phase selected on the basis of for example echo time, susceptibility or the size of features of interest. In other embodiments, the mask could be defined as if $|\phi_L(r)| = 0$ then $\phi_{MASK}(r) = 1$.

if $|\phi_L(r)| > 0$ then $\phi_{MASK}(r) = 1 - |\phi_L(r)|/\pi$. [7]

In yet other embodiments, the algorithm that produces the mask can be based either on theoretical grounds or on empirical grounds. For example, the predicted susceptibility effects can be used to calculate a mask or the mask may be simply found by repeated observation of certain known tissues while empirically modifying the mask with an eye towards optimizing contrast. The choice of phase mask can be made to enhance one tissue type or another. In one implementation, it can be used to separate two or more tissue types into different images where tissue A may be suppressed in one image and tissue B in another so as to give the appearance of an image dominated by tissue B in the former case and tissue A in the latter.

Step 160: The above phase mask, $\phi_{MASK}$, is then applied to the magnitude image by multiplying them together to form a susceptibility weighted image:

$$\rho_{swi}(r)=(\phi_{MASK}(r)*\rho_m(r) \quad [9]$$

A more general application of this concept is to perform the multiplication q times in the form:

$$\rho_{swi}(r)=(\phi_{MASK}(r))^{q}*\rho_m(r) \quad [10]$$

The choice of the mask multiplier, q, will depend, as is discussed below, on the signal-to-noise (SNR), the object size, the number of objects trying to be simultaneously seen and the value of the phase difference between features of interest, $\Delta\phi$, and requirements on the total time allocated for data acquisition. The choice of q can be derived from the contrast-to-noise (CNR) as follows for large values of SNR:

$$CNR(q)=SNR*(1-(1-|\Delta\phi|/\pi)^q)/\text{sqrt}(1+q^2/\pi^2) \quad [11]$$

$\Delta\phi$ is the phase difference, q is the number of multiplications, S is the signal in the magnitude image, and $\sigma$ is the noise in the magnitude image. Hence, SNR=S/$\sigma$ is the local signal-to-noise between the two tissues (assuming they both have the same magnitudes in this example; Eq. (11) can be modified to accommodate different signal intensities in each tissue). The numerator of Eq. (11) relates to the signal difference as a function of q in the susceptibility weighted image between two tissues with phase difference $\Delta\phi$ (note Eq. (7)). The denominator is the standard deviation of the noise in the susceptibility weighted image as a function of q. The denominator is determined by adding the noise in quadrature for the two terms. The variance (the square of the error term) then is just given by $\sigma^2$ $(1+q^2/\pi^2)$ where the factor of q comes from the fact that we multiplied the mask q times (and hence variance increases by $q^2$) and the factor of $1/\pi^2$ comes from the fact that we normalized the mask with $1/\pi$. The CNR as given in Eq. (11) therefore represents the signal difference (contrast) divided by the standard deviation of the noise.

Figure 2A:
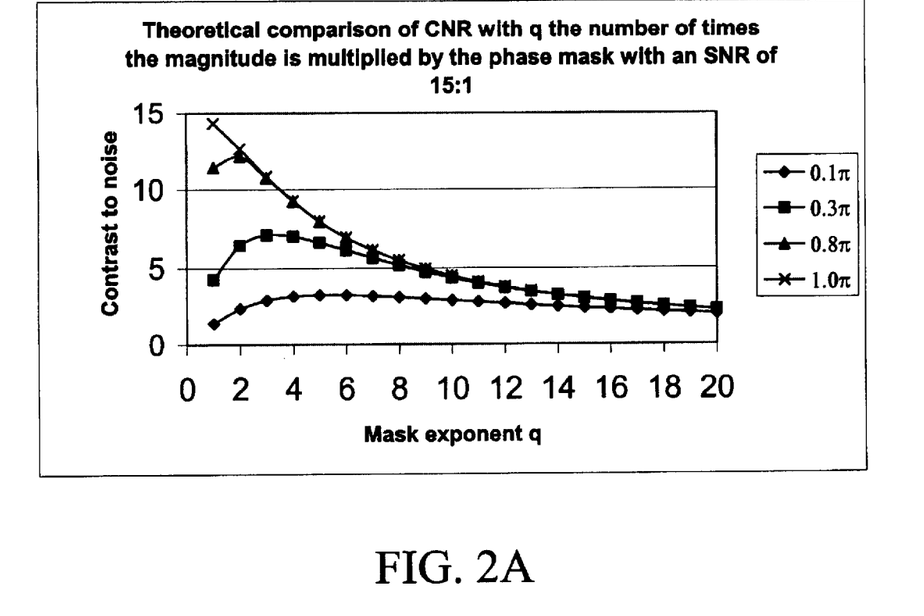
FIG. 2a is a plot of a theoretically predicted relation between CNR and the multiplication exponent q.

Referring to FIG. 2a, the relationship between contrast-to-noise and the multiplication exponent q computed according to Eq. (11) is shown. The relation is plotted for a number of different values of phase difference. The relation shown in FIG. 2a allows for the determination of the optimum q based on the phase difference and SNR. Conversely, given a target CNR, the relation allows for the determination of the combination of phase difference, SNR and q that may result in a final image with that target CNR.

Figure 2B:
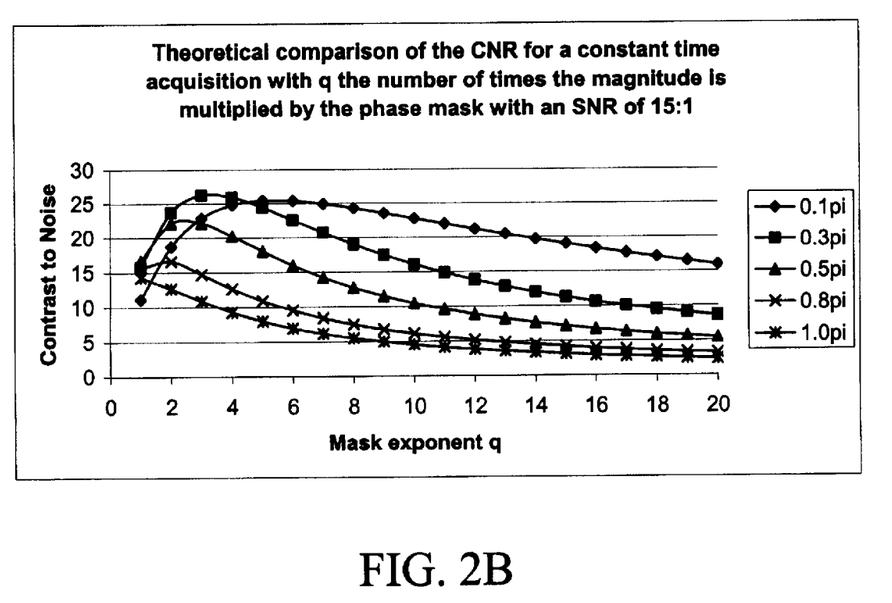
FIG. 2b is a plot of a theoretically predicted relation between CNR and the multiplication exponent q for a constant time experiment with signal averaging.

Another example of such CNR optimization relates to constant time experiments. Given a constant amount of time for data collection, CNR can be optimized with respect to the competing factors of phase difference versus signal averaging a number of data acquisitions. A shorter echo time TE leads to a larger number of repetitions of the scanning parameters so that the total time stays the same but the combined SNR goes up by a factor of sqrt($1/\alpha$). Here, $\alpha$ is the fractional reduction in the repeat time of the experiment from an experiment with a phase difference of $\pi$. That is, $\alpha=\Delta\phi/\pi$. A reduced TE changes the SNR per acquisition because the signal varies as exp($-TE/T_2^*$). For a TE reduction factor of $\alpha$, the combined signal increase is given by exp(($1-\alpha$)$TE/T_2^*$). This approximation does not include effects due to increases in the gradients needed to accommodate the reduced TE time. If TE becomes too short then the term sqrt($1/\alpha$) must be removed. Under these conditions, the analysis that lead to Eq. (11) is modified and produces:

$$CNR(q)=SNR*\text{sqrt}(1/\alpha)*\exp((1-\alpha)TE/T_2^*)*(1-(1-|\Delta\phi|/\pi)^q)/\text{sqrt}(1+q^2/\pi^2) \quad [12]$$

Referring to FIG. 2b, TE=$T_2^*$ is taken as the optimal choice for TE. Under the assumption of a constant time experiment, FIG. 2b reveals a TE chosen so that $\Delta\phi=\pi$ does not yield the highest CNR and that a better choice would be an echo time of 0.3 times this TE value using q=3. Even the case with 0.1 times this echo time yields a better CNR using q=5. Such a relationship is helpful in the design of the experiment. The SNR may drop at longer TE because of the T2* of the tissue and in such cases, by choosing a shorter TE, it is still possible to produce images with high CNR by taking advantage of signal averaging (i.e., taking the same acquisition time as with the longer TE scan) and the appropriate value of q.

Further considerations can be made if the object size is included. For example, if the size of the object is included, say as the radius, r (where r is measured in pixels), of a circular object, then a reasonable choice for q satisfies the relation $$4<r \text{ sqrt}(\pi) \text{ } CNR(q). \quad [13]$$

The factor 4 in Eq. (13) can be in the range from about 3 to about 5, depending on the expertise of the clinician interpreting the images. The more general expression replaces the term r sqrt($\pi$) with the term sqrt(A) where A is the area of the object being evaluated in square pixels. High resolution phase images will often allow for the separation of healthy tissue from diseased tissue because they often have different susceptibilities. For example, consider the case of atherosclerosis, where the blood vessel wall is affected. The diseased tissue may include: fatty plaque, fibrous plaque, hemorrhage, calcium deposits and vaso vasorum uptake of contrast agent.

Particular application of this method includes the following:

1) Increasing Contrast Between Water and Fat

In order to simulate the effects of a shorter echo time than can be collected with a given piece of equipment, the complex image from a sequence with an echo time of TE1 can be taken and divided into that of an image with an echo time of TE2 to get an equivalent echo time of TE2−TE1. For example, with TE2=10 ms and TE1=8 ms, the equivalent echo time is 2 ms. Collecting the data this way or with equipment that can actually acquire data with a TE=2 ms, the resulting phase images can be used to suppress fat in the brain or coronary arteries. Using the former approach, data are acquired with a resolution of 1×1×1 mm³ using a 3D gradient echo sequence. This value for TE is chosen to obtain fat about $\pi$ radians out of phase with water. The resulting phase images are well smoothed and clearly discriminate water and fat without the needed for any anti-aliasing programs. On the basis of Eq. (12) and since the phase theoretically lies between about 0.8$\pi$ to 0.9$\pi$ the optimal multiplication factor q should be 2. The fat signal in a T1 weighted sequence starts out being much brighter than the surrounding tissue. Therefore, the fat signal is reduced but not eliminated by the application of the mask once (i.e., q=1) and contrast with other brain tissues is poor. Applying the filter twice (i.e., q=2) improves CNR (actual results may be even better than predicted in Eq.(11) because of the increased signal of the fat relative to other tissue). Using a value of q=2 better suppresses the fat. This gives good contrast in the $T_1$ weighted images or in suppressing fat signals in angiographic images of the body.

2) Increasing Contrast Between Tissues With Different Amounts of Iron

The basal ganglia tend to gather iron over time. For example, the globus pallidus has larger iron content than neighboring tissues such as the caudate nucleus or putamen. For a TE of 80 ms, the phase of iron in brain tissue tends to be around $\pi/6$. This would suggest that q should be 6 or greater to obtain the best contrast in the susceptibility weighted image. However, even using a q=4 still gives good contrast so the method allows reasonable flexibility if there are other tissues or contrasts that one might wish to keep and yet still enhance the iron contrast as well. This method will enhance the boundaries between these tissues and the visibility of the structures. Further, if there is a disease process that increases the iron content of the tissue, this difference will be manifest as a darkening of the tissue with the increased iron content allowing the physician to better diagnose the condition. If the desire is to quantitate the amount of brain iron or just to see the boundaries between other tissues, the filtered phase image itself can also be used. At a TE of 80 ms, a heavier filter such as 96×96 or 128×128 should be used to remove background inhomogeneities. If the regions of interest are centrally located in the brain far from air tissue boundaries, then a filter of 32×32 can be used on each image. The filter can also be applied in three dimensions as a 32×32×32 filter.

Figure 3:
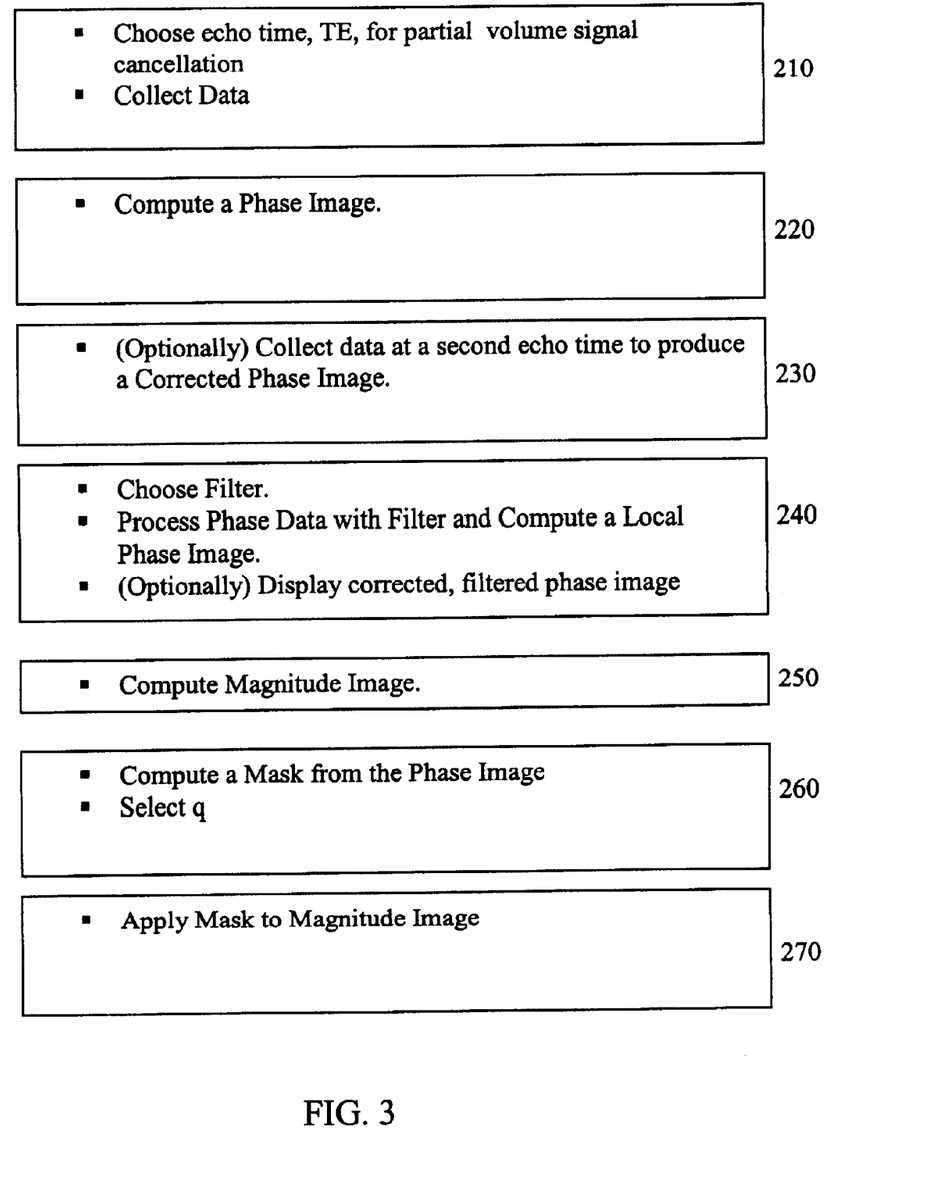
FIG. 3 is a diagram that outlines a method for MR imaging for visualizing features that are smaller than the resolution of the acquired MR data.

FIG. 3 outlines an MR imaging method 200. Typically, method 200 is used when features of interest are smaller than the resolution of the acquired data. Features that are physically smaller than the voxel size of the acquired data can lead to partial volume cancellations by which image contrast is increased. In addition to partial volume cancellations, such small features also impart information in the phase of the MR signal. Thus method 200 optimizes the parameters such as echo time, filter size, mask exponent, in order to optimize the final image contrast.

An MR imaging system collects the data (Step 210). Similar pulse sequences are used as for method 100. The echo time is chosen based on the optimal cancellation effect. This occurs when the phase difference is $\pi$ radians. However, it may not always be possible to collect data with the echo time associated with this value if this echo time is so long that little signal is left. In that case, a shorter echo time can be chosen and the number of multiplications is increased to accommodate the smaller cancellation and smaller phase effects. Even if the desired echo time is reached, a further enhancement of the contrast can be achieved using the mask multiplication described in method 100. These two features allow for a balance between the benefits of the contrast achieved from the phase image and the contrast achieved from any partial signal cancellations. Examples discussed below include separating arteries from veins and imaging small hemorrhages. The MR system applies standard data processing techniques to compute a phase image, $\phi(r)$, across the sample (Step 220).

The partial volume effects are optionally further highlighted by collecting data at two echo times TE1 and TE2 (Step 230). The phase from echo one at TE1 is multiplied by TE2/TE1 to create a predicted phase $\phi_{Pred}(r)$ at TE2. This phase is then subtracted from the phase $\phi_{Exp}(r)$ of the second echo at TE2 to give a corrected phase image $\phi_{CORR}(r)$:

$$\phi_{CORR}(r)=\phi_{Exp}(r)-\phi_{Pred}(r) \tag{14}$$

This operation gives zero phase in all areas of the image except where partial volume effects occur. In areas where partial volume effects occur, the phase behavior is non-linear. For example, for a vessel parallel to the field in a voxel with 50% signal coming from gray matter and 50% from the blood at an echo time of 25 ms at 1.5T, the phase of the resulting vector is 45° (this is because the phase of the blood is 90° but the phase of the gray matter is zero). At TE=50 ms, the blood signal will dominate and the phase will be 180°. If the blood has less than 50% contribution then the phase will be zero. In either case, when TE is doubled from 25 to 50 ms the phase does not double (hence, it is non-linear in its behavior). On the other hand, the material that sees a background field inhomogeneity has a linear phase behavior and all of these terms vanish. If this step is applied, the resulting phase image $\phi_{CORR}(r)$ replaces the original phase image in the following process.

An appropriate filter size is computed and a data processing algorithm applies this filter to the phase image (or the phase corrected image) producing a local phase image, $\phi_L(r)$ (Step 240). The filter removes the phase contributions from the field inhomogeneity $\Delta B_z^0(r)$ and furthermore the filter reduces most of the nonlocal contributions to the phase image. These can include eddy current phase effects as well as shifts caused by a poorly centered echo.

The raw data is used to compute a magnitude image $\rho_m(r)$. (Step 250)

Using the filtered local phase image, a mask, $\phi_{MASK}(r)$ is calculated and the mask exponent q is computed in a similar fashion as described in methods 100 (Step 260).

The mask is applied to the magnitude image to form a final susceptibility weighted image (Step 270).

$$\rho_{swi}=(\phi_{MASK})^q*\rho_m(r) \tag{15}$$

Applications of this method include:

1) Imaging Veins

Veins have a change in susceptibility compared to arteries and surrounding tissue. When veins are smaller than a voxel, and echo time increases toward $\pi$ radians, the signal from the veins begins to cancel that from the surrounding tissue. This makes them visible (they appear dark) compared to arteries which often appear isointense or bright in the images. Small veins (less than a pixel in size) parallel to the field will be best seen with echo times of 40 to 50 ms. Small veins perpendicular to the main field will be ideally enhanced at 1.5 T with an echo time of about 80 to 100 ms. For vessels that are between 0.2 to 0.5 mm in diameter, for example, an in-plane resolution of 0.5 mm×0.5 mm to 1.0 mm×1.0 mm would be a good choice. For 3 T, the echo time would be reduced to about 40 to about 50 ms. For smaller vessels a higher resolution should be used. Diseased tissue can extract more oxygen from the blood making the level of deoxyhemoglobin in the veins increase and hence its susceptibility increase. This would then make the perpendicular vessels visible at the shorter echo times from about 40 to 50 ms and would be an indicator of a problem in the tissue drained by those veins that otherwise would normally not have been seen until the later echo times. On the other hand, since the brain contains vessels of varying size and orientation, it is safe to apply a large q on the order of 4 to 6 to show good contrast from vessels with smaller phase changes or partial volume effects which also reduce the local phase. One can also process a series of images to view images with different values of q and look for different structures of interest from image to image.

2) Imaging Microhemmorrhage

When a clot or hemorrhage occurs in the tissue, the susceptibility goes up dramatically, perhaps by as much as a factor of 4 to 10 or more. This means that the cancellation effects can be seen at much shorter echo times and for much smaller sized objects. For example, a sphere of volume ¼ that of a pixel would be seen best at an echo time of 40 to 80 ms if it had the same susceptibility of normal veins. However, if its susceptibility goes up by a factor of 4 the echo time could be reduced by a factor of 4. Alternatively, if the echo time remains large, then the volume of the object required to cause significant signal loss will also go down by a factor of roughly 4. The multiplication factor q will be chosen based on the resulting phase in the region of interest. Often small hemorrhages are visible with this method that may not otherwise be visible with conventional technology.

Figure 4:
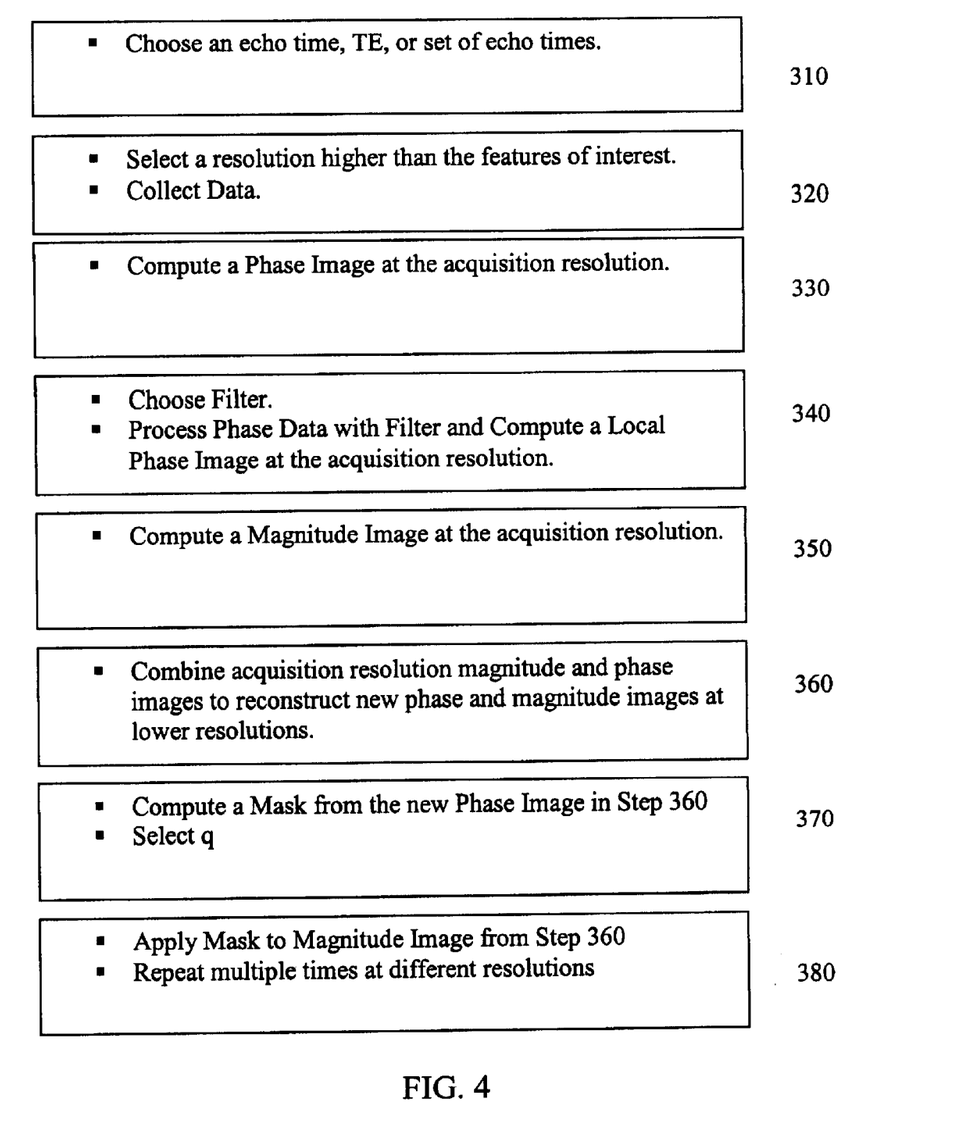
FIG. 4 is a diagram that outlines a method for MR imaging for visualizing features with a high resolution acquisition and simultaneously taking the same data and reconstructing images at lower resolution than the resolution of the acquired data.

FIG. 4 outlines an MR imaging method 300 that uses phase information typically induced by susceptibility effects to varying degrees and also uses image reconstruction at a variety of resolutions less than or equal to the acquisition resolution. Data are collected at one or more echo times to enhance features of interest.

An optimum value or set of values for TE is chosen (Step 310). An MR imaging system collects the data for a specified TE using a single echo scan or a range of TE values using a multi-echo scan at an acquisition resolution chosen to be higher than the resolution of some of the features of interest (Step 320). Examples which are discussed below are imaging small vessels, imaging hemorrhage or local mineralization. The MR system applies standard data processing techniques to compute a phase image, $\phi(r)$, across the sample (Step 330). An appropriate filter size is computed and a data processing algorithm applies this filter to the phase image producing a local phase image, $\phi_L(r)$ (Step 340). The filter removes the phase is contributions from the field inhomogeneity $\Delta B_z^0(r)$ and furthermore the filter reduces most of the nonlocal contributions to the phase image. The filter size is chosen based on the echo time and the extent and spatial variations in the background field. The slower the spatial variation, the smaller the filter size required to correct the data.

The MR system applies standard data processing techniques to compute a magnitude image, $\rho_m(r)$, at the acquisition resolution (Step 350). The information in the local phase image and the magnitude image are combined to form a complex image, $\rho(r)=\rho_m(r)^* \exp(i\phi_L(r))$, and a new phase and magnitude image are reconstructed at a lower resolution than the acquisition resolution (Step 360). In other embodiments, the complex image can be formed from the original magnitude and the original phase images by $\rho(r)=\rho_m(r)^* \exp(i\phi(r))$. The choice will depend on which of the two images yield the best contrast-to-noise. For example, in some cases, by constructing the complex image using the local phase image the effects of background fields are removed while the effects of the local sources of signal change from blood vessels or hemorrhage are not altered. The particular lower resolution chosen would correspond to a resolution comparable to some feature of interest. Typically, this reconstruction includes vector summing the magnitude and phase of each voxel at the acquisition resolution until the lower resolution voxel size is attained. This reduction from a high resolution to a low resolution image is affected by filtering the complex data. For example, to collapse the image from a 0.5 mm×0.5 mm image to a 1.0 mm×1.0 mm image can be done in several ways. One way uses a sliding window filter defined by the weighting coefficients w(i)=0.5 for i taking on the values 1 and 2 in the formula: $\rho_{new}(m)=w(1)\rho(m)+w(2)\rho(m+1)$ for all values of m from 1 to n (where there are n pixels in the image). As discussed above, $\rho(m)$ and $\rho(m+1)$ are complex valued. When m=n, $\rho(n+1)$ is set to zero a and w(1) is set to unity. This is a sliding filter. Only the odd points in m may be taken hence reducing the matrix size to n/2 points to save space. Variants of this filter such as w(1)=0.25, w(2)=0.5, w(3)=0.25 can be used with the modified formula $\rho_{new}(m)=w(1)\rho(m)+w(2)\rho(m+1)+w(3)\rho(m+2)$ for all values of m from 1 to n (where there are n pixels in the image). When m=n−1, $\rho(n+1)$ is set to zero and w(1) and w(2) are set to 0.5 When m=n, $\rho(n+1)$ and $\rho(n+2)$ are set to zero and w(1) is set to unity. This one-dimensional filter can be applied also as a 2D filter or 3D filter by simply applying the filter in both or all three directions. All such filtered images can then be viewed separately as if they had been acquired with the lower resolution. The advantage of viewing the data this way is that each scale that the image is viewed at will reveal unique features related to the scale (or size) of the pixels. Normal venous blood vessels will be best revealed when the pixel size is roughly 4 times smaller than the resolution (or voxel size). Small hemorrhages may be best seen when the voxel volume is ten times larger than the hemorrhages (depending on the age of the hemorrhage).

A mask $\phi_{MASK}(r)$ is computed and a mask exponent q is computed (Step 370). The phase mask can be applied to the reconstructed magnitude image, $\rho_{m\_new}(r)$ to form a final susceptibility weighted image (Step 380) as described in method 100 or 200.

$$\rho_{swi}(r)=(\phi_{MASK}(r))^{q*}\rho_{m\_new}(r) \quad [16]$$

This can be done using either the high resolution original phase images or the lower resolution images. The advantage of the latter is there will be an improvement in signal-to-noise in the phase images (but a loss of resolution and hence a loss of phase information). On the other hand, the original phase will have a better defined set of edges and better defined phase and may in some circumstances yield better phase masked information in the images. Applications of such a method include:

1) Imaging Veins

Veins have a change in susceptibility compared to arteries and surrounding tissue. When veins are smaller than a voxel, and echo time increases toward π radians, the signal from the veins begins to cancel that from the surrounding tissue. This makes them uniquely visible (they appear dark) compared to arteries which often appear isointense or bright in the images. Small veins (less than a pixel in size) parallel to the field will be best seen with echo times producing phase differences of π or approximately 40 ms to 50 ms. Small veins perpendicular to the main field will be ideally enhanced at 1.5T with an echo time of 80 to 100 ms. For vessels that are between 0.2 to 0.5 mm in diameter, for example, an in-plane resolution of 0.5 mm×0.5 mm to 1.0 mm×1.0 mm would be a good choice. However, veins can be as small as 50 microns in size. By imaging at as high a resolution as possible, for example at 250 microns in humans or 100 microns say in small animals such as rats or mice, and then reconstructing a series of images with lower resolutions such as 500 microns, 1 mm and 2 mm, many different features can be revealed in the different images. This is akin to using a microscope to focus in on a structure of interest. Everything else may become blurry for a given focus, but what is blurry in one image will be sharper in a different resolution image. The optimal q value will depend on how the phase changes for the smaller voxel size. Generally, to obtain the best CNR, as the resolution decreases (the voxel size increases) the q value will need to be increased. However, the larger CNR of the lower resolution images will partly offset the need to use a larger q value. If the need is to see contrast typically then as long as CNR is greater than 4 that q value will suffice.

2) Imaging Microhemmorrhage

When a clot or hemorrhage occurs in the tissue, the susceptibility goes up dramatically, perhaps by as much as a factor of 4 to 10 or more. This means that the cancellation effects can be seen at much shorter echo times and for much smaller sized objects. For example, a sphere of volume ¼ that of a pixel would be seen best at an echo time of 40 to 80 ms if it had the same susceptibility of normal veins. However, if its susceptibility goes up by a factor of 4, the echo time could be reduced by a factor of 4. Alternatively, if the echo time remains large, then the volume of the object required to cause significant signal loss will also go down by a factor of 2 to 4. Often many small hemorrhages are visible with this method that may otherwise not be visible using conventional imaging methods.

Again, clots of different sizes can be enhanced in terms of their visualization by varying the resolution in the image as described above. Hemorrhages can occur at all levels from a few dozen microns to on the order of a millimeter. By imaging at as high a resolution as possible, for example at 250 microns in humans or 100 microns say in small animals such as rats or mice, and then reconstructing a series of images with lower resolutions such as 500 microns, 1 mm and 2 mm, many different features can be revealed in the different images. Again the optimal q value will depend on the available CNR, phase and imaging time available. Hemorrhages on the order of a cubic mm may be best viewed with a resolution of 2 mm while a small hemorrhage on the order of 250 microns may be best viewed with a resolution of 0.5 mm.

In other embodiments, the above methods can be applied to produce a series of images. From such a series, a minimum intensity projection may be used to form a new composite image. Once a series of images has been created either with or without phase masking and with or without reconstructing with different resolutions, a minimum intensity projection may be used to best visualize a connected series of vessels or other structures or just as a means of viewing all the information in a given area relative to the anatomy better. This method takes a series of images and searches along a set of rays in a given direction and chooses the smallest value along that ray to write out to a new projected image. This can be applied to the original magnitude images or the phase processed images. It can be applied to any image at any echo time. It can also be applied to the phase images themselves.

The above described methods are another means by which to visualize what structures are being enhanced by the phase masking process. For example, the contiguity of vessels may be seen in these images or the location of hemorrhages relative to the basal ganglia or the venous vasculature may be seen in this way.

A number of embodiments of the invention have been described. Nevertheless, it will be understood that various modifications may be made without departing from the spirit and scope of the invention. Accordingly, other embodiments are within the scope of the following claims.

What is claimed is:

1. A method of MR imaging, comprising:
   obtaining A magnitude image;
   obtaining a phase image;
   computing a phase image mask using the phase image;
   applying the phase image mask to the magnitude image a number q times; and
   selecting q by computing CNR as a function of q.

2. The method of claim 1 wherein CNR is computed as a function of SNR and $\Delta\phi$.

3. The method of claim 2 wherein
   $\Delta\phi$ is the phase difference between water and fat.

4. The method of claim 2 wherein
   $\Delta\phi$ is the phase difference between tissues with different amounts of iron.

5. The method of claim 2 wherein $$CNR(q)=SNR*(1-(1-|\Delta\phi|/\pi)^q)/\sqrt{1+q^2/\pi^2}.$$

6. The method of claim 1, 2, or 5
   wherein selecting q further comprises using a function dependent on the size of a feature of interest.

7. The method of claim 6 wherein
   selecting q such that sqrt(A) CNR(q) is greater than a value in the range from about 3 to about 5 where A is the area of the feature of interest measured in square pixels.

8. The method of claim 1 comprising:
   selecting a filter for reducing nonlocal contributions to the phase image;
   computing a local phase image by filtering a first phase image with said filter to reduce nonlocal contributions on said image; and
   wherein computing a phase image mask further comprises using the local phase image.

9. The method of claim 1 or 8 comprising
   obtaining said magnitude and phase image by selecting a first echo time that results in partial volume cancellation of features of interest.

10. The method of claim 9 comprising
    obtaining images of veins.

11. The method of claim 9 comprising
    obtaining images of microhemorrage.

12. The method of claim 9 comprising:
    obtaining a second phase image by selecting a second echo time that results in partial volume cancellation of features of interest;
    computing a corrected phase image by using the first and second phase images; and
    wherein computing the phase image mask further comprises using the corrected phase image.

13. The method of claim 1 comprising
    selecting an acquisition resolution such that the resolution is higher than the size of a feature of interest; and
    acquiring magnitude and phase data at the acquisition resolution.

14. The method of claim 13 wherein
    obtaining a magnitude and obtaining a phase image comprises reconstructing a magnitude and a phase image at a lower resolution than the resolution of the acquired data.

15. The method of claim 14 wherein
    reconstructing a magnitude and a phase image comprises using the magnitude data and the phase data.

16. The method of claim 14 comprising
    selecting a filter for reducing nonlocal contributions to the phase data;
    computing local phase data by filtering the phase data with said filter to reduce nonlocal contributions on the phase data; and
    wherein reconstructing the magnitude and the phase image comprises using the magnitude data and the local phase data.

17. A method of MR imaging comprising:

computing CNR as a function of q, SNR, and $\Delta\phi$; and selecting q, SNR and $\Delta\phi$ to produce a desired CNR.

18. The method of claim 17 comprising selecting an echo time to produce the selected SNR or $\Delta\phi$.

19. The method of claim 17 comprising selecting a set of echo times to produce the selected SNR or $\Delta\phi$.

20. The method of claim 17, 18, or 19 wherein $$CNR(q)=SNR*(1-(1-|\Delta\phi|/\pi)^q)/\text{sqrt}(1+q^2/\pi^2).$$

21. The method of claim 17 wherein the desired CNR is defined such that sqrt(A) CNR(q) is greater than a value in the range from about 3 to about 5 where A is the area of the feature of interest measured in square pixels.

22. The method of claim 17 wherein

CNR is dependent on the number of data acquisitions; and selecting a number of data acquisitions to produce the desired CNR.

23. The method of claim 22 comprising for a given total data acquisition time, selecting a number of data acquisitions.

24. The method of claim 22 wherein

CNR is computed according to $CNR(q)=SNR*\text{sqrt}(1/\alpha)*\exp((1-\alpha)TE/T_2^*)*(1-(1-|\Delta\phi|/\pi)^q)/\text{sqrt}(1+q^2/\pi^2)$ wherein $\alpha=\Delta\phi/\pi$.

25. The method of claim 17 wherein

SNR and $\Delta\phi$ depend on partial volume cancellations.

26. A method of MR imaging, comprising:

obtaining a magnitude image;

obtaining a phase image;

computing a phase image mask using the phase image;

applying the phase image mask to the magnitude image a number q times;

selecting q by computing CNR as a function of q selecting an acquisition resolution such that the resolution is higher than the size of a feature of interest; and wherein obtaining a magnitude and obtaining a phase image comprises reconstructing a magnitude and a phase image at a lower resolution than the resolution of the acquired data.

* * * * *